United States Patent
Rye et al.

[11] Patent Number: 5,792,941
[45] Date of Patent: Aug. 11, 1998

[54] MEASUREMENT OF SURFACE TENSION AND VISCOSITY BY OPEN CAPILLARY TECHNIQUES

[75] Inventors: Robert R. Rye, Albuquerque; Frederick G. Yost, Cedar Crest, both of N. Mex.; J. Adin Mann, Jr., Cleveland Heights, Ohio

[73] Assignee: Sandia Corporation, Albuquerque, N. Mex.

[21] Appl. No.: 727,072

[22] Filed: Oct. 8, 1996

[51] Int. Cl.$^6$ .............................. G01N 11/00; G01N 13/00
[52] U.S. Cl. ........................................ 73/53.01; 73/64.48
[58] Field of Search ............................. 73/54.01, 54.02, 73/54.07, 54.13, 53.01, 64.48, 64.51

[56] References Cited

U.S. PATENT DOCUMENTS

| | | | |
|---|---|---|---|
| H337 | 10/1987 | Matta | 73/54.07 |
| 1,637,386 | 7/1927 | McClain | 73/54.01 |
| 2,054,438 | 9/1936 | Natelson | 73/64.51 |
| 2,295,710 | 9/1942 | Bostwick | 73/54.01 |
| 3,513,092 | 5/1970 | Matherne | 210/658 |
| 3,864,263 | 2/1975 | Jethwa et al. | 73/61.1 C |
| 4,534,211 | 8/1985 | Molina | 73/53.01 |
| 5,200,248 | 4/1993 | Thompson et al. | 428/131 |
| 5,491,642 | 2/1996 | Wormell et al. | 364/509 |

*Primary Examiner*—Hezron E. Williams
*Assistant Examiner*—Jay L. Politzer
*Attorney, Agent, or Firm*—George H. Libman

[57] ABSTRACT

An open-channel capillary is provided, having preferably a v-shaped groove in a flat wettable surface. The groove has timing marks and a source marker in which the specimen to be tested is deposited. The time of passage between the timing marks is recorded, and the ratio of surface tension $\gamma$ to viscosity $\mu$ is determined from the equation given below:

$$z^2 = K(\alpha,\theta)[h_0]\left[\frac{\gamma}{\mu}\right]t$$

where $h_0$ is the groove depth, $\alpha$ is the groove angle, $\theta$ is the liquid/solid contact angle, and t is the flow time. It has been shown by the inventors that the kinetics are only at most a weak function of $K(\alpha,\theta)$; moreover, a wide range of theoretical assumptions show comparable numerical values for $K(\alpha,\theta)$. $\gamma+\mu$ and $h_0$ are the only parameters. With the depth of the groove being an experimentally controllable parameter, the ratio of $\gamma+\mu$ is the only free parameter. The value of $\gamma+\mu$ can be determined from plots of $z^2v.$ t by taking the slope of the curve for measured value of $h_0$.

15 Claims, 5 Drawing Sheets

MEASUREMENT OF SURFACE TENSION AND VISCOSITY BY OPEN CAPILLARY TECHNIQUES

FIELD OF THE INVENTION

The field of this invention relates to techniques and equipment for simplified measurement of surface tension and viscosity individually, as well a ratio of the two.

BACKGROUND OF THE INVENTION

For the last 60 years, research has been conducted on the wetting of rough surfaces and the infiltration of porous media by liquids. The liquid flow into porous media has received more attention. Models of wetting kinetics on rough surfaces have been empirical or thermodynamic in origin.

A rough surface can be conceptually thought of as a three-dimensional network of connected open capillaries that would have measurable root mean square (rms) amplitude, rms slope, etc. Therefore, a rough surface can be viewed as a network of contiguous valleys through which the liquid is drawn by capillary forces. A desirable object was to relate these simple measures of surface roughness to actual wetting behavior so that surfaces could be engineered for specific application. Various experimentation has gone on with regard to kinetics of capillary flow and closed capillaries. One of the leaders in this field was E. W. Washburn, whose early work in horizontal cylindrical capillaries was published in the *Physics* Review in 17, 273 (1921). The work of Washburn and others showed that the length of a liquid column z entering the cylindrical capillary followed relatively simple kinetics, $$z^2 = \cos(\theta) \cdot [\gamma r/\mu] t \quad (1)$$

where $\gamma$ is the liquid surface tension, r is the capillary radius, $\theta$ is the contact angle, and $\mu$ is the bulk liquid viscosity. The Washburn approach has been applied to capillary spreading into the two-dimensional capillary form between flat plate and into square capillaries.

The shortcomings of the closed capillary techniques have been that many fluids to be tested are opaque or are not compatible with the tube materials which would allow observation of the movement of the fluid through the tube. The use of closed capillaries also induced significant measurement errors in that measurement of movement of the fluid was only reliably possible at the point of entrance into the tube and at the point of exit. Some materials, due to incompatibilities with transparent tubes or due to the physical properties and appearance of the material to be tested, did not avail themselves readily to a closed tube capillary testing technique. Thus, the apparatus and method of the present invention was developed to allow a simple way to consistently determine the surface tension to viscosity ratio. By producing a simple tool to test for these properties individually or as a ratio, a standard could be developed to test materials to make sure that they perform within a predetermined range of parameters. This has many applications in many different industries, including semiconductor manufacturing where adhesives are used to hold chips to substrates during chip manufacturing. Applications also involve uses in secondary oil recovery, liquid-metal penetration into fine scale castings, soldering, and brazing, and various other adhesive processes used for bonding. In many of these applications, the ratio of surface tension to viscosity ($\gamma/\mu$) is important. Current techniques involve independent determination of these properties. In applications where the liquids are opaque, complications have ensued with currently available techniques for measuring surface tension and viscosity.

Accordingly, the object of the invention is to provide a method and technique for using open-channel capillaries such as found in v-shaped grooves in a flat wettable surface to determine reliably the ratio of surface tension to viscosity. The technique can be used to test a given product for properties falling within a given specification. In such applications, the object of the apparatus and method is to provide a reliable quality control instrument. Alternatively, the surface tension itself can be independently obtained from use of the same tool.

SUMMARY OF THE INVENTION

An open-channel capillary is provided, having preferably a v-shaped groove in a flat wettable surface. The groove has timing marks and a source marker in which the specunen to be tested is deposited. The time of passage between the timing marks is recorded, and the ratio of surface tension y to viscosity, u is determined from the equation given below:

$$z^2 = K(\alpha, \theta)[h_0][\gamma/\mu] t$$

where $h_0$ is the groove depth, $\alpha$ is the groove angle, $\theta$ is the liquid/solid contact angle, and t is the flow time. It has been shown by the inventors that the kinetics are only at most a weak function of $K(\alpha, \theta)$; moreover, a wide range of theoretical assumptions show comparable numerical values for $K(\alpha, \theta)$, as described in the specification hereinafter. $\gamma/\mu$ and $h_0$ are the only parameters. With the depth of the groove being an experimentally controllable parameter, the ratio of $\gamma/\mu$ is the only free parameter. The value of $\gamma/\mu$ can be determined from plots of $z^2$ v. t by taking the slope of the curve for measured value of $h_0$, or $_1$. More simply, by measuring the time required for the material to transit two distance marks.

DETAILED DESCRIPTION OF THE DRAWINGS

DETAILED DESCRIPTION OF THE PREFERRED EMBODIMENT

Figure 1:
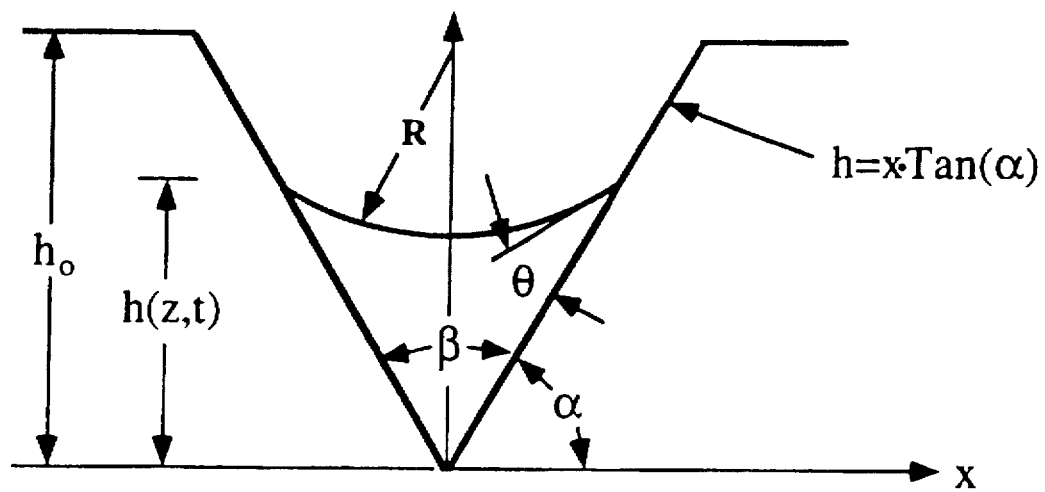
FIG. 1 is a schematic representation of the groove spreading experiment giving the experimental and geometric parameters.
Figure 1:
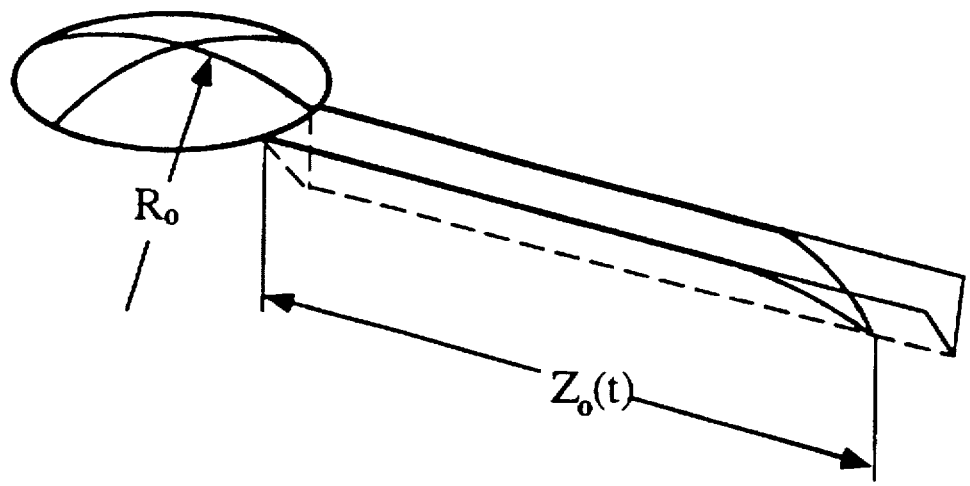

Treatments of the kinetics of capillary flow in closed capillaries have been studied for over 50 years. For horizontal cylindrical capillaries, Washburn and Rideal using slightly different approaches weree able to show that the length of liquid column, z, entering the cylindrical capillary followed relatively simple kinetics, $z^2=\cos(\theta)\cdot[\gamma r/\mu]t$ where $\gamma$ is the liquid surface tension, r is the capillary radius, $\theta$ is the contact angle, and $\mu$ is the bulk liquid viscosity. Despite some problems the basic Washburn equation has remained the basis of nearly all treatments of capillary dynamics. Fisher and Lark reported exact agreement with the Washburn equation for cyclohexane using a wide range of capillary diameters, but a slight deviation in the case of water for which they resorted to a nonchanging contact angle of 30°; even for water, however, the basic $z \propto t^{1/2}$ dependence predicted by the Washburn equation was observed. The same basic Washburn approach has been applied to capillary spreading into the two-dimensional capillary formed between flat plates, and to square capillaries. Even in the case of radial flow into a flat two-dimensional slit from a point source, where Washburn kinetics was not followed over the entire range, the kinetics follow an approximate $t^{1/2}$ dependence after a short induction period.

In contrast to flow in closed capillaries, this invention utilizes the flow kinetics of organic alcohols over a small a wide range of surface tension to viscosity ratios ($\gamma/\mu$), groove angles ($\theta$) and groove depths ($h_o$), to show that the spreading length, z, of liquid in open surface V-grooves follows a square root of time dependence with the same basic form as for closed cylindrical capillaries: $z^2=K(\alpha,\theta)\cdot[\gamma h_o/\mu]t$. Scaling the slopes of linear plots of z vs $t^{1/2}$ with the basic Washburn parameters $(\gamma h_o/\mu)^{1/2}$ accounts for the majority of the difference between the different alcohol spreading systems; the experimental kinetics are only weakly dependent on the $K(\alpha,\theta)$ term for the range of $\alpha,\theta$ values studied.

Two theoretical models were compared to these experimental kinetics. One is a detailed similarity solution based on a model using the condition of mass balance, the Laplace equation, static contact angles, and Poiseuille flow, which through its dependence on the Laplace equation requires a curved liquid surface at the threshold of the liquid flowing down the column. The second, more similar to the original Washburn approach, is based on static contact angles, Poiseuille flow, and the total interfacial energy change as the liquid flow down the groove, a model which allows capillary flow independent of the shape of the liquid surface. Both approaches yield the same basic relationship $z^2=K(\alpha,\theta)\cdot[\gamma h_o/\mu]t$ for the spreading kinetics, but with different forms for the geometry term $K(\alpha,\theta)$. Thus, testing of these theoretical formulations is reduced to comparing experimental and theoretical values for $K(\alpha,\theta)$. Such comparison, however, based on both scaling and numerical values yields no significant differentiation between experiment and theory or between theories.

EXPERIMENTAL SECTION

V-grooves, FIG. 1, were cut in six different 2.5 cm×2.5 cm×0.3 cm pieces of polished Cu with carefully ground and polished machine cutting tools having included angles of 30°, 60°, and 90°. Each hard tool was weighted for pressing into the soft Cu positioned, and then drawn across the surface in a single pass such that each sample contained one example of each groove angle intersecting at a common point. The effect was more of pressing the image of the nonrotating, hard cutting tool into the soft Cu than of cutting. Since the pressing action resulted in surface eruption of Cu at the edges of the groove, all samples were polished subsequent to groove cutting to produce more accurate triangular grooves relative to the polished surface.

The depth of the resulting grooves were determined by two techniques: a Dektak-8000 profilometer and a WYCO (MHT-II) vertical scanning interferometer. The interferometer is an optical instrument which produces a two-dimensional view of a segment of the groove with an associated depth scale. The scanning needle of the Dektak profilometer had a cone-angle of 60° and could be expected to yield accurate profiles and depths for only the 90° grooves. The recorded Dektak data is a convolution of the actual groove shape and the probe tip shape. To obtain accurate groove depths for the 30° and 60° grooves, dental impression material (hydrophilic vinyl polysiloxane, Dentsply International, Milford, Del.) was used to produce images of the grooves for profilometry. Profilometer traces for representative 30°, 60°, and 90° grooves and their dental images are given in FIG. 2, and the groove depths obtained by both methods for all samples are given in Table 1. As expected, the 90° groove and its dental image give nearly identical measures of both shape and depth; the groove depths obtained by the two methods differ by less than 5%. For the 60° grooves, profilometry gives approximately the same depths as interferometry, but the trace of the sides of the groove are effectively linear suggesting that the side wall shape is an artifact resulting from the use of a profilometer needle with a cone angle of 60°. For the 30° grooves there is considerably larger variation, in some cases, in the groove depth, Table 1, between the Dektak and WYCO values and a greater distortion of the dental image shape, FIG. 2, suggesting that the WYCO optical data may be more accurate for the narrow 30° grooves. As a result the groove depths given in Table 2 for use in data reduction refer to an average value of the Dektak and WYCO data for the 60° and 90° grooves but to only the WYCO data for the 30° grooves. Both the Dektak data and the WYCO data show that the grooves are reasonably accurate triangular grooves but with a slight asymmetry due to either a slight asymmetry in grinding the cutting tools or vertical positioning and a rounding of the groove bottom which is obvious in the case of the 90° grooves.

Figure 2:
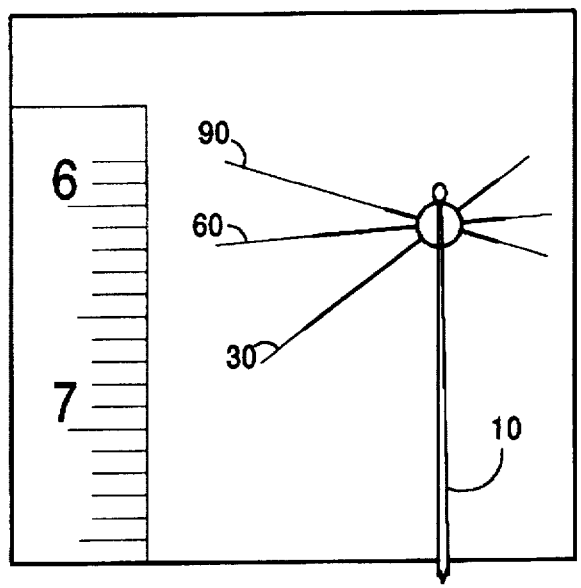
FIG. 2 shows an image of one frame obtained dunng spreading of diethylene glycol.

While we will continue to differentiate between experiment results in terms of 30°, 60°, and 90° grooves, it is clear from the curves in FIG. 2 that there is considerable deviation from the shape of the tool used to create the grooves: the grooves show asymmetry and in some cases have clear rounded bottoms, and the included angles $\beta$ are larger than the tool angles of 30°, 60°, and 90°. Given the limitations of the WYCO and Dektak data, it is not possible to obtain more accurate information about shape, except possibly for the 90° grooves. The combination of WYCO and Dektak data is expected to give a reasonably accurate measure of the groove depths, and the Dektak is expected to provide a reasonably accurate value for the position of the groove edges and thus the groove width. If we make the crude assumption that the groove widths and depths define symmetrical triangular grooves, a more realistic approximation of the groove angles $\beta$ can be obtained. Such values are listed in Table 1.

The organic alcohols listed in Table 2 were used as received. A small amount of the fluorescent dye coumarin was added to each of the liquids for contrast. Irradiation of the sample with UV light during an experiment greatly increased the contrast between the fluorescing liquid in the groove and the Cu substrate. Between runs, each sample was first scrubbed with soapy water and then ultrasonically rinsed sequentially in water, acetone, and methanol. Values for the viscosities and surface tensions of the alcohols were obtained from the Beilstein Handbook of Organic Chemistry. For 1,4-butanediol single values of surface tension 40.3 dyn/cm (22° C.) and viscosity 0.761 P (24.9° C.) were reported. For cyclohexanol, the average of four entries in the range from 20° to 30° C. was 34.05 dyn/cm, while the average of the three most recent values for the viscosity at 25° C. was 0.585 P. For 1-butanol, the average of two entries at 25° C. to yielded 24.3 dyn/cm for the surface tension and an average of five entries at 25° C. yielded 0.0258 P for the viscosity. For 2-octanol, the average of two entries yielded a surface tension of 26.2 dyn/cm (20° C.) and a viscosity of 0.0641 P (25° C). For diethylene glycol single entries listed values of 48.5 dyn/cm for the surface tension (25° C.) and 0.30 P for the viscosity (25° C ). For 1-heptanol, five entries were averaged to give a surface tension of 26.9 dyn/cm (20° C.) and two entries were averaged to give a viscosity of meter scale filled an appreciable fraction of the field of view. A Sony video recorder fitted with time base electronics was used to record both an individual spreading event along with a time mark recorded in units of 1/30 s; the time marks were accurate to approximately 1/100 s. In a typical experiment a few video frames of the sample were obtained with normal lighting for calibration before starting a spreading run with only UV lighting by using a hypodermic needle 10 to place a small drop of alcohol at the intersection of the three grooves 30, 60, 90, the same drop served as the source for spreading in all three grooves.

TABLE 1

Groove Depths and Angle β for Six Polished Cu Samples.

| | 30° grooves | | | 60° grooves | | | 90° grooves | | |
|---|---|---|---|---|---|---|---|---|---|
| Cu | groove depth, µm | | groove | groove depth, µm | | groove | groove depth, µm | | groove |
| sample | Dektak | WYCO | angle β, deg | Dektak | WYCO | angle β, deg | Dektak | WYCO | angle β, deg |
| 1 | 89.1 | 85.7 | 42 | 58.8 | 50.7 | 71 | 33.2 | 32.5 | 122 |
| 2 | 72.6 | 92.9 | 50 | 56.9 | 53.3 | 79 | 40.4 | 40.4 | 119 |
| 3 | 66.6 | 74.4 | 49 | 57.4 | 57.7 | 69 | 37.7 | 39.6 | 109 |
| 4 | 110.0 | 98.7 | 45 | 89.0 | 92.8 | 77 | 47.4 | 48.2 | 124 |
| 5 | 95.3 | 98.6 | 50 | 83.1 | 89.9 | 79 | 45.0 | 45.9 | 125 |
| 6 | 100.6 | 98.3 | 40 | 74.9 | 85.5 | 71 | 41.3 | 42.5 | 119 |

TABLE 2

Experimental Parameters and Experimental and Calculated Kinetic Rate Data for Sample 4

| liquid | γ/µ cm/s | contact angle θ, deg | meas groove angle, deg | groove height, µm | exptl rate, cm/s$^{1/2}$ | exptl | $K(\alpha,\theta)^{1/2}$ theory eq 20 | eq 11 | eq 13 |
|---|---|---|---|---|---|---|---|---|---|
| 30° Groove: Multiple Liquids | | | | | | | | | |
| 1,4-butanediol | 59.5 | 29 | 45 | 98.7 | 0.188 | 0.245 | 0.356 (0.343) | 0.282 (0.311) | 0.291 (0.319) |
| cyclohexanol | 58.2 | 6 | 45 | 98.7 | 0.188 | 0.247 | 0.369 (0.372) | 0.301 (0.330) | 0.325 (0.348) |
| 1-butanol | 941 | 6 | 45 | 98.7 | 0.824 | 0.270 | 0.369 (0.372) | 0.301 (0.330) | 0.325 (0.345) |
| 2-octanol | 408 | <2 | 45 | 98.7 | 0.521 | 0.259 | 0.363 (0.369) | 0.297 (0.327) | 0.326 (0.350) |
| diethylene glycol | 162 | 33 | 45 | 98.7 | 0.293 | 0.231 | 0.347 (0.335) | 0.273 (0.302) | 0.250 (0.309) |
| 1-heptanol | 489 | <2 | 45 | 98.7 | 0.545 | 0.249 | 0.363 (0.369) | 0.297 (0.327) | 0.326 (0.350) |
| 60° Groove: Multiple Liquids | | | | | | | | | |
| 1,4-butanediol | 59.5 | 29 | 77 | 91 | 0.180 | 0.244 | 0.313 (0.345) | 0.219 (0.253) | 0.226 (0.262) |
| cyclohexanol | 58.2 | 6 | 77 | 91 | 0.200 | 0.275 | 0.331 (0.394) | 0.248 (0.275) | 0.275 (0.302) |
| 1-butanol | 941 | 6 | 77 | 91 | 0.861 | 0.294 | 0.331 (0.394) | 0.248 (0.275) | 0.275 (0.302) |
| 2-octanol | 408 | <2 | 77 | 91 | 0.574 | 0.298 | 0.320 (0.384) | .0241 (0.270) | 0.277 (0.303) |
| diethylene glycol | 162 | 33 | 77 | 91 | 0.227 | 0.187 | 0.296 (0.334) | 0.204 (0.242) | 0.210 (0.250) |
| 1-heptanol | 489 | <2 | 77 | 91 | 0.591 | 0.281 | 0.296 (0.354) | 0.241 (0.270) | 0.277 (0.303) |
| 90° Groove: Multiple Liquids | | | | | | | | | |
| 1,4-butanediol | 59.5 | 29 | 124 | 47.8 | | | 0.0 (0.277) | 0.0 (0.189) | 0.0 (0.194) |
| cyclohexanol | 58.2 | 6 | 124 | 47.8 | 0.100 | 0.190 | 0.212 (0.345) | 0.174 (0.227) | 0.194 (0.254) |
| 1-butanol | 941 | 6 | 124 | 47.8 | 0.411 | 0.194 | 0.212 (0.345) | 0.174 (0.227) | 0.194 (0.254) |
| 2-octanol | 408 | <2 | 124 | 47.8 | 0.282 | 0.202 | 0.197 (0.349) | 0.166 (0.220) | 0.199 (0.257) |
| diethylene glycol | 162 | 33 | 124 | 47.8 | | | 0.0 (0.252) | 0.0 (0.169) | 0.0 (0.172) |
| 1-heptanol | 489 | <2 | 124 | 47.8 | 0.304 | 0.199 | 0.197 (0.349) | 0.166 (0.220) | 0.199 (0.257) |

*The values in parentheses were calculated using assumed values of 30°, 60°, and 90° instead of the measured values in column 4.

0.0551 P (25° C). The surface tension to viscosity ratios obtained from these values are given in the second column of Table 2.

FIG. 2 shows a rendition of spreading experiments recorded in real time through use of a 512×512 pixel charge coupled device (CCD) camera attached to a zoom lens with a magnification such that the sample and a reference centi- Subsequently, an Image Pro system with frame grabber was used to capture individual frames as TIFF files for further processing. An example of processing of one such frame is shown in FIG. 2 for diethylene glycol spreading in the grooves of Cu sample 4. The contrast was first adjusted to emphasize the centimeter scale used for length calibration. The contrast of the same video frame was readjusted to emphasize the fluorescing liquid. Thus, although it was not necessary because of the stability of the video magnification, the data contains the capability for frame-by-frame calibration. The lower number in each image is the time stamp in hours:minutes:seconds:number of frames. The 30°, 60°, and 90° grooves, the end of the spreading liquid, and the edge of the source drop are noted on the images. Spreading lengths, or the distance between the source drop and the spreading front in the groove, were measured using Mocha and Optimas image analysis software.

THEORETICAL SUMMARY

The fundamental relationship of $z^2=K(\alpha,\theta)\cdot[\gamma h_o/\mu]t$ can be deduced by dimensional analysis and the factor $f(\alpha,\theta)$ cataloged. However, this gives no insight into the surface chemistry of the flow process. We focus on two models. One is based on the original Washburn/Rideal approach and the second follows the more detailed approach of Romero and Yost.

EXPERIMENTAL RESULTS AND INTERPRETATION

Figure 3:
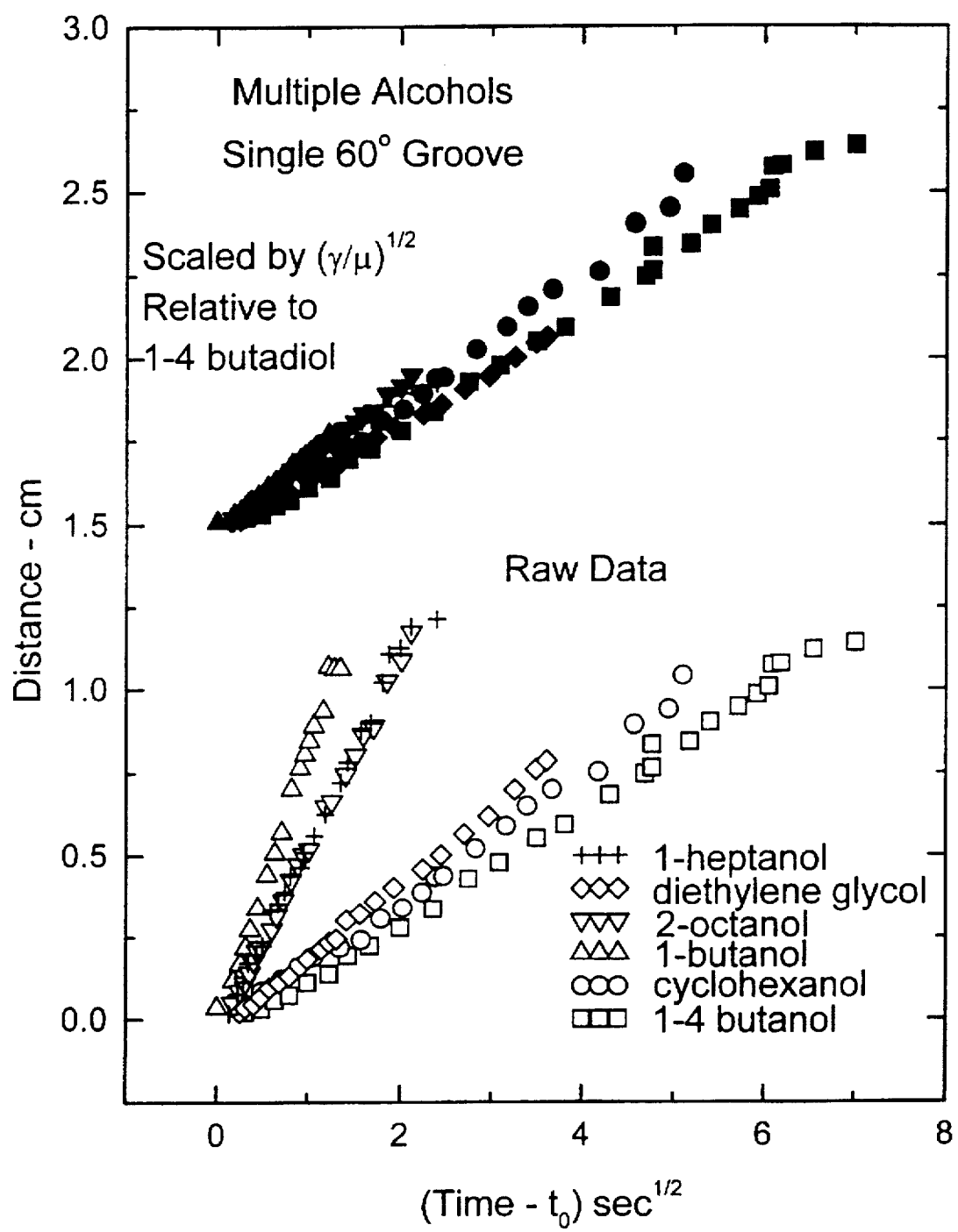
FIG. 3 shows the spreading distance z plotted as the square root of time for six alcohols flowing in the same 60° V-groove.
Figure 4:
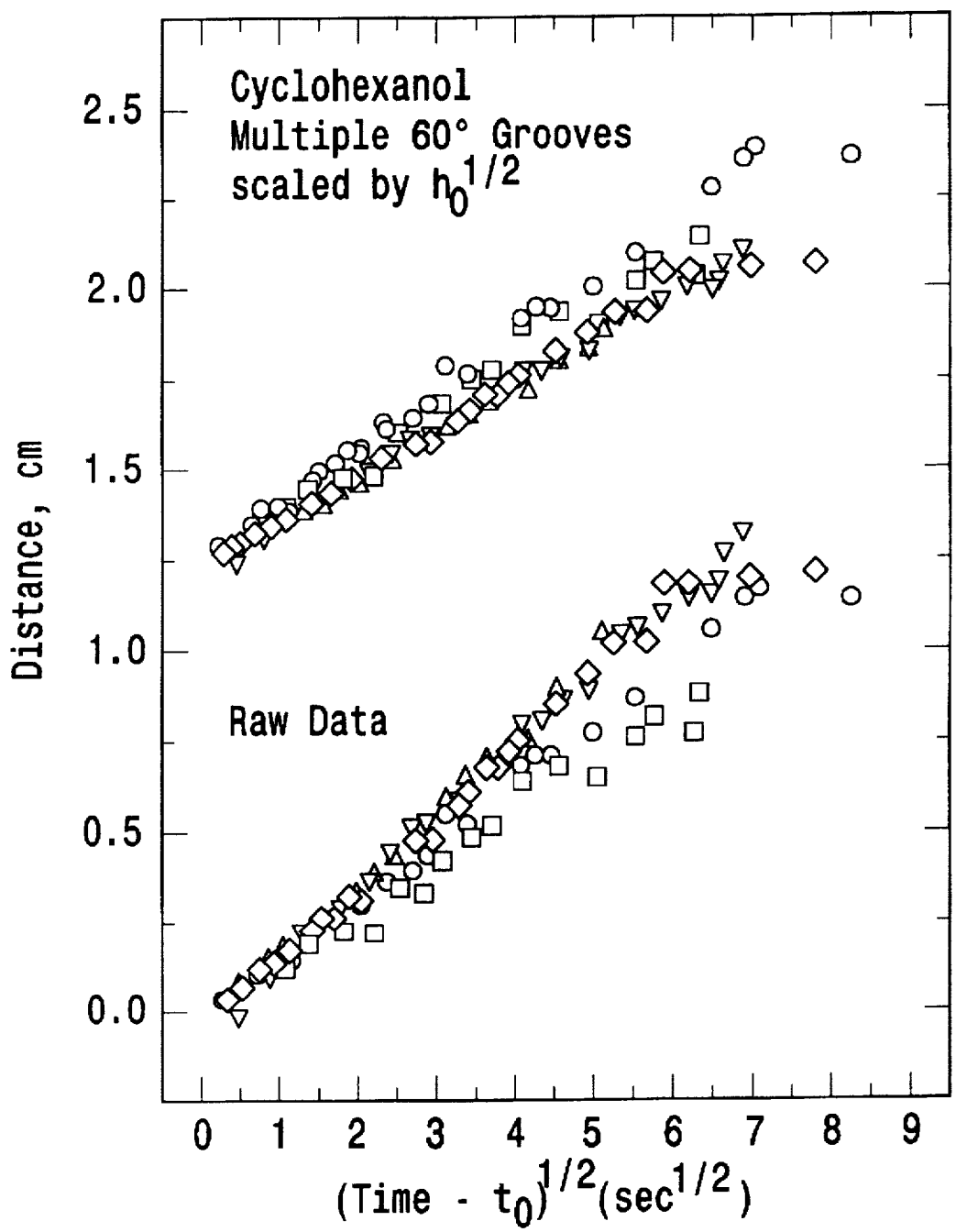
FIG. 4 shows the spreading distance plotted as the square root of time for cyclohexanol flowing in six different 60° V-grooves.

For a series of single frames such as shown in FIG. 2 the measured kinetic data consisted of the time and the distance z measured from the edge of the source drop to the point in the groove where fluorescence could no longer be detected. The initial time $t_0$ was taken from the first frame in which a trace of liquid could be detected in the groove, usually determined with single frame resolution (1/30 s). Such spreading distance data is shown plotted in the lower portion of FIG. 3 vs the square root of the spreading time $(t-t_0)^{1/2}$ for six different alcohols flowing in the same 60° groove. All follow a $t^{1/2}$ dependence for all frames where measurable liquid could be detected in the groove, a result consistent with all theoretical approaches. This is a universal result of this study and true for all combinations of liquid and substrate for which flow occurred. Least squares fits to the experimental data yielded slopes, generally with standard deviations of ~0.005, whose values are listed in the sixth column of Table 2. The seventh column, labeled experimental $K(\alpha,\theta)^{1/2}$ is the result of dividing the experimental slope, column 6, by the factor $(\gamma h_o/\mu)^{1/2}$ obtained from the experimental values in columns 2 and 5. The remaining columns, are calculated values of $K(\alpha,\theta)^{1/2}$ using the contact angles in column 3 and the approximate groove angles in column 4. For the values given in parentheses the design angles of 30°, 60°, and 90°.

TABLE 3

Spreading Rate Data for 1-Butanol on Six Different Cu Samples, Each with 30°, 60°, and 90°

| Groove Angle | Sample | exptl rate | $h_o$, µm | rate $(h_{c4c}/h_o)$ | % deviation from mean |
|---|---|---|---|---|---|
| 30° | C1C | 0.6763 | 87.4 | 0.7371 | −12. |
| " | C2C | 0.7757 | 82.8 | 0.08694 | +3.7 |
| " | C3C. | 0.7273 | 70.5 | 0.8834 | +5.4 |
| " | C4C | 0.8240 | 104 | 0.8240 | −1.7 |
| " | C5C | 0.8376 | 97.0 | 0.8673 | +3.5 |
| " | C6C | 0.8285 | 99.5 | 0.8470 | +1.1 |
| 60° | C1C | 0.6119 | 54.7 | 0.7888 | −5.3 |
| " | C2C | 0.6537 | 55.1 | 0.8396 | +0.82 |
| " | C3C | 0.6661 | 57.6 | 0.8368 | +0.48 |
| " | C4C | 0.8610 | 90.9 | 0.8610 | +3.4 |
| " | C5C | 0.7875 | 86.5 | 0.8072 | −3.1 |
| " | C6C | 0.8109 | 80.2 | 0.8633 | +3.7 |
| 90° | C1C | 0.2999 | 32.8 | 0.3620 | −10.4 |

TABLE 3-continued

Spreading Rate Data for 1-Butanol on Six Different Cu Samples, Each with 30°, 60°, and 90°

| Groove Angle | Sample | exptl rate | $h_o$, µm | rate $(h_{c4c}/h_o)$ | % deviation from mean |
|---|---|---|---|---|---|
| " | C2C | 0.3745 | 40.4 | 0.4073 | +0.86 |
| " | C3C | 0.3822 | 38.6 | 0.4253 | +5.3 |
| " | C4C | 0.4110 | 47.8 | 0.4110 | +1.8 |
| " | C5C | 0.4037 | 45.5 | 0.4137 | +2.5 |
| " | C6C | 0.3779 | 41.9 | 0.4036 | −0.05 | were as $K(\alpha,\theta)$ is relatively insensitive to values of $\alpha,\theta$. This relative insensitivity of $K(\alpha,\theta)$, the only factor which differentiates theories, places strenuous conditions on the quality of the experimental data. As a measure of precision, the rate data for one alcohol, 1-butanol, on six different Cu samples has been collected in Table 3. The raw experimental slopes for the 30°, 60°, and 90° grooves for all samples are contained in the second column. All the experimental approaches given above agree that in this situation the experimental slopes should depend only on $h_o^{1/2}$. Accordingly, all the experimental data in Table 3 were scaled, column 4, by the square root of the heights given in column 3 using sample C4C as a reference.

Figure 5:
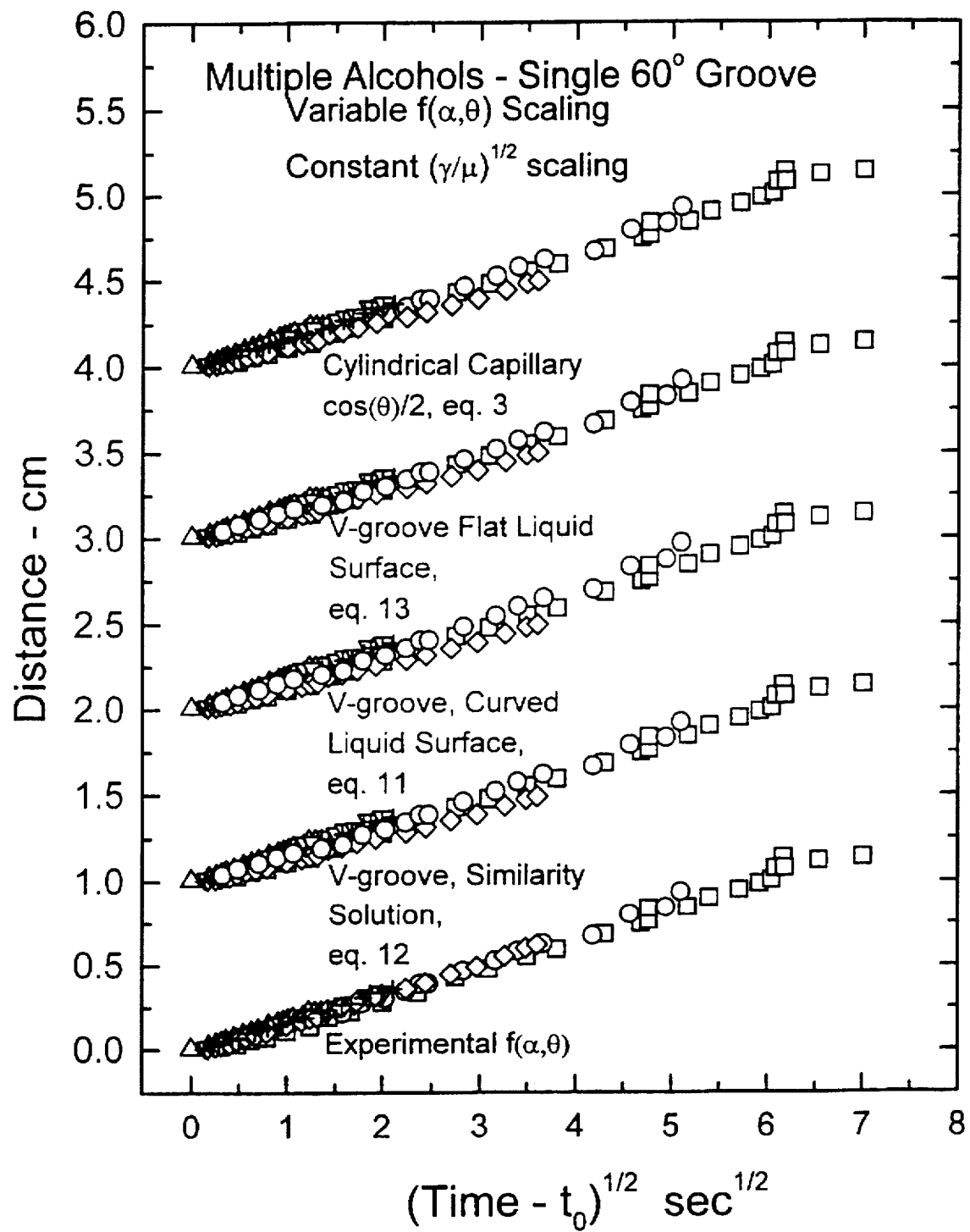
FIG. 5 shows the spreading distance for the data in FIG. 5 plotted as the square root of time after scaling.

However, while tests of scaling behavior are necessary when treating capillary spreading kinetics, it is not sufficient to probe the differences between theoretical descriptions, despite the apparent major differences in the form of the $K(\alpha,\theta)$ term given by different assumptions of the physical characteristics of the liquid in the channel during theoretical calculations. To directly compare the effect of these different forms for the $K(\alpha,\theta)$ term, we have used the data for multiple alcohols spreading in the same 60° groove given in FIG. 3, a system for which all the theoretic approaches agree restricts the active parameters to only $K(\alpha,\theta)$ and $\gamma/\mu$. Five versions of this data are given in FIG. 5 scaled relative to 1-butanol; common $\gamma/\mu$ scaling was used for all but different $K(\alpha,\theta)$ scaling according to the different theoretical approaches given in the Theoretical Summary section as well as the experimental value of $K(\alpha,\theta)$. Thus, the only difference between the five sets of scaled curves is the method of obtaining $K(\alpha,\theta)$. The experimental value of $K(\alpha,\theta)$ was included simply to illustrate the level of agreement to be expected with a proper value of $K(\alpha,\theta)$. From bottom to top in FIG. 5, the plots reflect decreasing levels of mathematical complexity (decreasing complexity of the $K(\alpha,\theta)$ term) keyed to the theoretical calculations. The experimental and theoretical values for the $K(\alpha,\theta)$ terms are given in the last four columns of Table 2. It is clear, as far as scaling is concerned, that all models are equally valid, even to the extreme case of applying the cylindrical capillary case, $\cos(\theta)/2$, to the V-groove data. Scaling, of course, probes the ratios within a set of values and not the values themselves.

DISCUSSION

From comparison of the experimental kinetic data for spreading of alcohols in well-characterized V-grooves with a variety of theoretical models, which range from the detailed hydrodynamic model of Romero and Yost to simple models based on a Washburn approach, we have established that the spreading kinetics are well represented by a simple model of the general form $$z^2=K(\alpha,\theta)[h_o][\gamma/\mu] \qquad (2)$$

This form was first established in 1921 by Washburn and Rideal and experimentally verified for cylindrical capillaries by Fisher and Lark, for the specific case of horizontal cylindrical capillaries. All models considered here and the experimental data are in agreement with this form, with differences only as to the form of the $K(\alpha,\theta)$ term. However, it should be clear from the values given in Table 2 that experimentally $K(\alpha,\theta)$ is relatively insensitive to values of $\alpha$ and $\theta$, a conclusion consistent with experiment and both models.

Common to all the theoretical approaches is the assumption of Poiseuille flow, an assumption which leads to the $[\gamma h_0 t/\mu]^{1/2}$ kinetic dependence which is common to all the theories and to experiment. A second common feature is the use of a static advancing contact angle, an assumption which in all theories correctly predicts the small contact angle dependence of the rate. However, it should also be pointed out that all three theories are relatively insensitive to changes in $\alpha$ and $\theta$. The differences between the theoretical approaches is in the details of the liquid shape in the threshold region. Clearly, these differences are small suggesting that the detailed geometry of the liquid surface is relatively unimportant in determining the capillary flow kinetics. This would further imply that hydrodynamic properties are important in determining flow kinetics in open capillaries at least for those cases where flow does occur. The interesting caveat to this is that groove geometry, in controlling the shape of the liquid meniscus, may play a central rode in determining whether flow does or does not occur, but when flow does occur the rate is relatively insensitive to changes in the groove shape. The main conclusion must be that the basic Washburn approach established in 1921 is fully capable of capturing the essential surface chemistry involved in capillary flow in open triangular grooves. Further, the numerical predictions from this simple approach are indistinguishable from much more complex and detailed hydrodynamic models for the range of variables available in the present study.

SUMMARY AND CONCLUSIONS

For flow of alcohols in open V-shaped capillary grooves cut into polished Cu surfaces the follouing conclusions can be drawn.

1. For capillary flow, experiment and three different models, even the most physically unreal, agree on kinetics of the form $z^2 = K(\alpha,\theta)[\gamma h_0/\mu]t$, where $\gamma$ is the liquid surface tension, $h_0$ is the groove height, $\mu$ is the liquid viscosity, and $K(\alpha,\theta)$ is a geometric term containing the groove angle $\alpha$ and the contact angle $\beta$.
2. For the theoretical approaches the forms of the $K(\alpha,\theta)$ terms are drastically different, but their limiting behavior as $\alpha \to \theta$ are the same, resulting in a constraint of $\alpha > \theta > 0$ for flow to occur, and the experimental and calculated values of $K(\alpha,\theta)$ are similar.
3. Only Poiseuille flow and static advancing contact angles are assumed.
4. Detailed geometry and contact angle together determine whether flow does or does not occur but play only, a minor role in the kinetics once flow occurs.
5. On the basis of the present experimental data, no distinction can be made between the theoretical models. Even the simple Washburn-based approaches contain the essential surface chemistry and predict, within experimental capability, the detailed kinetics, but only the approach of Romero and Yost has the refinement potential to calculate more accurately the profile shape.

Figure 6:
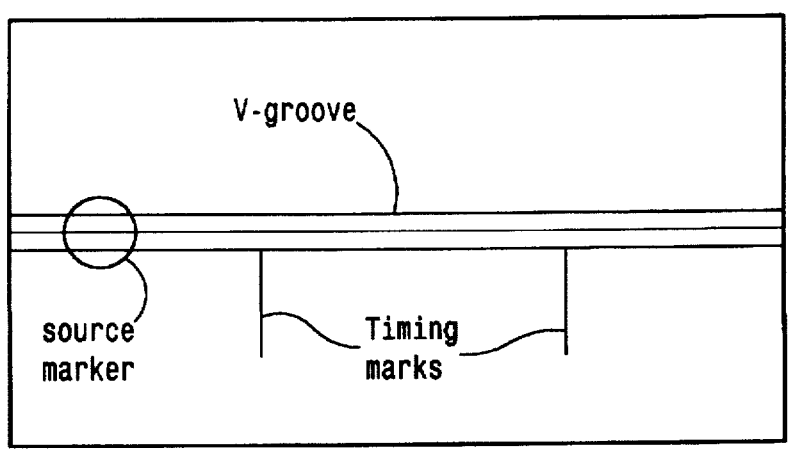
FIG. 6 is a plan view of an apparatus employing the technique of the present invention.
Figure 7:
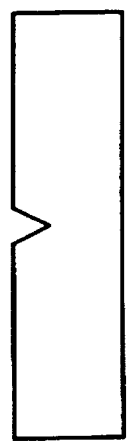
FIG. 7 is a section view through the apparatus showing the V-shaped groove.

As can be seen by the above description, the measurement technique for determining the ratio of the surface tension to viscosity involves the use of equation 2 in the apparatus as illustrated in FIGS. 6 and 7. The sample is deposited where indicated in the groove at the position called "source marker." The material of construction for the apparatus shown in FIGS. 6 and 7 can be a material compatible with the liquid to be tested, and in the preferred embodiment comprises, as illustrated in FIGS. 6 and 7, of a V-shaped groove in a flat wettable surface. Kinetics for a capillary flow indicate that equation 2 represents the relationship between the variables for determining the ratio of the surface tension to viscosity by determining the time and distance from the equation, with measurements using the apparatus of FIGS. 6 and 7. The groove illustrated in these figures can be produced from photolithography in silicon and then coated with any depositable material. The groove can also be pressed into the substrate plate using a preformed tool, or can be cut into the substrate using a sharp preformed tool. The method begins with the placement of a small drop of liquid in the source marker, which consists of a small hollow. Liquid is then drawn down the V-groove by capillary action. This movement can be videotaped in conjunction with a timing mark on the video. Individual video frames and paired values of the distance z and time t can then be obtained. A linear plot of $z^2$ versus t is made from which the value of surface tension versus viscosity can be obtained from the slope, using a predetermined value for $h_0$ as the total depth of the groove, which is known.

Accordingly, the instrument as depicted in FIGS. 6 and 7 can be readily used for quality control by measuring the arrival times of the liquid at two measured distance marks and calculating the slope from the single pair of point. A specification can easily be set up for a given material as to the time required for it to pass between the two timing marks as the quality standard itself.

What is disclosed is a simple and quick measurement technique to determine the surface-tension-to-viscosity ratio. The grooves used in the device should be substantially horizontal, and the cross-section between the distance marks should be substantially uniform. The same device, however, can be used in an equally simple manner to determine the surface tension by itself. The apparatus of FIGS. 6 and 7 can be placed substantially vertically in the liquid and the liquid will rise in the groove until gravitational forces on the liquid drawn up into the groove are balanced by the capillary forces. The surface tension, being directly proportional to the height of the capillary column when the capillary and gravitational forces are in balance, gives the apparatus shown in FIGS. 6 and 7 additional utility in measuring directly the surface tension by itself. This technique give the same results as prior designs using the capillary rise method for surface tension, performed in closed cylindrical capillaries. However, by the use of an open channel of known configuration, two simple measurements can be made to allow a computation of the ratio of surface tension to viscosity and also to allow determination of the surface tension and, hence, the viscosity as independent quantities. By virtue of using the open surface groove technique, as described, the limitations of prior designs to transparent liquids and transparent capillaries, when using the closed tube design, are eliminated. With this technique and device, a broad range of different liquids can be readily tested. The inaccuracies of closed tube designs, even putting aside the limitations of material compatibilities and lack of transparency in the tested fluids, are eliminated in the surface groove technique described.

While the cross-sectional shape of the preferred embodiment has been illustrated as a V-shaped groove, other groove cross-sections, such as circle segments, square or rectangular, are within the purview of the invention.

The foregoing disclosure and description of the invention are illustrative and explanatory thereof, and various changes in the size, shape and materials, as well as in the details of the illustrated construction, may be made without departing from the spirit of the invention.

What is claimed is:

1. A method of determining physical properties of a liquid, comprising:

providing a base having an open channel having a predetermined cross-section and height;

identifying a fixed distance in said channel;

depositing a sample of the liquid to be tested into said channel at a point outside said fixed distance;

measuring the time the liquid takes to flow through said fixed distance; and computing the ratio of surface tension to viscosity of the liquid from a plot of said fixed distance squared versus the measured time for the liquid to flow across said fixed distance.

2. The method of claim 1, further comprising:

using the slope of a line representing the square of said fixed distance plotted against time to determine the ratio of surface tension to viscosity.

3. The method of claim 1, further comprising:

holding said base substantially horizontal.

4. The method of claim 2, further comprising:

holding said base substantially horizontal.

5. The method of claim 1, further comprising:

using a V-shaped cross-section for said channel.

6. The method of claim 4, further comprising:

using a V-shaped cross-section for said channel.

7. The method of claim 1, further comprising:

providing a small hollow outside said fixed distance for receiving said initial deposit of the liquid.

8. The method of claim 6, further comprising:

providing a small hollow outside said fixed distance for receiving said initial deposit of the liquid.

9. The method of claim 7, further comprising:

using video with a time display to record progress of the liquid across said fixed distance;

examining individual video frames to determine the time for liquid to flow between said distance markings.

10. The method of claim 8, further comprising:

using video with a time display to record progress of the liquid across said fixed distance;

examining individual video frames to determine the time for liquid to flow between said distance markings.

11. The method of claim 1, further comprising:

producing said channel by pressing into said base using a preformed tool.

12. The method of claim 11, further comprising:

producing said channel in a copper base.

13. The method of claim 6, further comprising:

producing said channel by photolithography in silicon, coated with a depositable material.

14. The method of claim 6, further comprising:

producing said channel by pressing into said base using a preformed tool.

15. The method of claim 6, further comprising:

using a V-shaped cross-section for said channel.

* * * * *

UNITED STATES PATENT AND TRADEMARK OFFICE
CERTIFICATE OF CORRECTION

PATENT NO. : 5,792,941
DATED : August 11, 1998
INVENTOR(S) : Rye et al.

It is certified that error appears in the above-identified patent and that said Letters Patent is hereby corrected as shown below:

Column 4, line 12, change "Profilometer traces...Figuure 2 and the" to --The--.

Column 4, line 26, delete "Figure 2,".

Column 4, line 40, delete "from the curves of Figure 2".

Signed and Sealed this

Twenty-third Day of February, 1999

Attest:

Q. TODD DICKINSON

*Attesting Officer*   Acting Commissioner of Patents and Trademarks